United States Patent [19]

Nakagawa et al.

[11] 4,068,076

[45] Jan. 10, 1978

[54] 5-(1-HYDROXY-2-(HETEROCYCLIC AMINO))ETHYL-8-HYDROXY-3,4-DIHYDROCARBOSTYRIL DERIVATIVES

[75] Inventors: Kazuyuki Nakagawa, Tokushima; Shiro Yoshizaki, Naruto; Kaoru Tanimura, Tokushima; Shigeharu Tamada, Tokushima, all of Japan

[73] Assignee: Otsuka Pharmaceutical Co., Ltd., Tokyo, Japan

[21] Appl. No.: 701,268

[22] Filed: June 30, 1976

Related U.S. Application Data

[63] Continuation-in-part of Ser. No. 536,704, Dec. 26, 1974, Pat. No. 3,975,391.

[30] Foreign Application Priority Data

| Dec. 26, 1973 | Japan | 49-4192 |
|---|---|---|
| May 22, 1974 | Japan | 49-58316 |
| May 27, 1974 | Japan | 49-60003 |
| May 27, 1974 | Japan | 49-60004 |
| May 27, 1974 | Japan | 49-60005 |
| May 27, 1974 | Japan | 49-60006 |

[51] Int. Cl.$^2$ .................. C07D 413/06; C07D 401/06
[52] U.S. Cl. ................... 544/128; 260/268 BQ; 260/287 K; 260/288 CE; 260/289 K; 424/248.54; 424/250; 424/258
[58] Field of Search ............ 260/288 CE, 247.2 A, 260/268 BQ

[56] References Cited

U.S. PATENT DOCUMENTS

| 3,444,173 | 5/1969 | Goldman | 260/268 BQ |
|---|---|---|---|
| 3,975,391 | 8/1976 | Nakagawa et al. | 260/288 CE |
| 3,994,901 | 11/1976 | Nakagawa et al. | 260/288 CE |

OTHER PUBLICATIONS

Morrison et al.; Organic Chemistry (1969) pp. 666, 866, 567.
Chodorekar et al., J. Med. Chem., vol. 15 (1972) pp. 49–57.
J. Med. Chem. vol. 15, pp. 260–266 (1972).
Imp. Chem. Ind. Ltd.; Chem. Abs. vol. 621, 16212e (1965).

*Primary Examiner*—Donald G. Daus
*Assistant Examiner*—M. C. Vaughn
*Attorney, Agent, or Firm*—Sughrue, Rothwell, Mion, Zinn and Macpeak

[57] ABSTRACT

5-[1-hydroxy-2-(heterocyclic amino)]ethyl-8-hydroxy-3,4-dihydrocarbostyril derivatives represented by the formula (I)

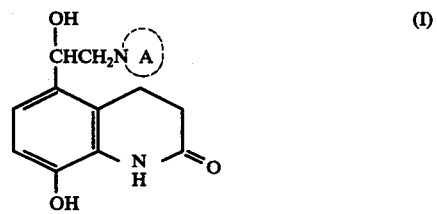

wherein A, when taken together with the nitrogen atom to which it is attached, forms a 6-membered substituted or unsubstituted heterocyclic ring containing 1 or 2 nitrogen, or oxygen atoms as hetero atoms, the pharmaceutically acceptable acid addition salts thereof, and a process for preparing the above compounds.

4 Claims, No Drawings

5-(1-HYDROXY-2-(HETEROCYCLIC AMINO))ETHYL-8-HYDROXY-3,4-DIHYDROCARBOSTYRIL DERIVATIVES

CROSS REFERENCE

This application is a continuation-in-part application of co-pending application Ser. No. 536,704 filed Dec. 26, 1974, now U.S. Pat. No. 3,975,391.

BACKGROUND OF THE INVENTION

1. Field of the Invention

This invention relates to novel carbostyril derivatives and a process for preparing the same. More particularly, this invention relates to novel 5-[1-hydroxy-2-(heterocyclic amino)]-ethyl-8-hydroxy-3,4-dihydrocarbostyril derivatives and a process for preparing the same.

2. Description of the Prior Art

It is well known that certain carbostyril derivatives exhibit useful pharmaceutical activities. Representative compounds of this type have been disclosed in *Journal of Medical Chemistry*, Vol. 15, No. 3, pp. 260–266 (1972), Japanese Patent Publication No. 38789/1971 and Chemical Abstracts, 62, 16212e (1965), etc. However, these prior art references do not teach that the compounds having a [1-hydroxy-2-(heterocyclic amino)]-ethyl group at the 5-position of the carbostyril moiety possess an excellent β-adrenoreceptor stimulating activity.

It has been found that 8-hydroxy-3,4-dihydrocarbostyril derivatives having a [1-hydroxy-2-(heterocyclic amino)]ethyl group at the 5-position of the carbostyril moiety and pharmaceutically acceptable acid addition salts thereof possess a β-adreno-receptor stimulating activity, and therefore, are useful as a therapeutic agent such as a bronchodilator, a peripheral vasodilator and an antihypertensive agent, particularly for treating bronchial asthma.

SUMMARY OF THE INVENTION

The present invention provides novel 5-[1-hydroxy-2-(heterocyclic amino)]ethyl-8hydroxy-3,4-dihydrocarbostyril derivatives having the formula (I)

wherein A, when taken together with the nitrogen atom to which it is attached, form a 6-membered substituted or unsubstituted heterocyclic ring containing 1 or 2 nitrogen, or oxygen atoms as hetero atoms.

This invention also provides a process for preparing the above 5-[1-hydroxy-2-(heterocyclic amino)]ethyl-8-hydroxy-3,4-dihydrocarbostyril derivatives represented by the formula (I)

wherein A, when taken together with the nitrogen atom to which it is attached, form a 6-membered substituted or unsubstituted heterocyclic ring containing 1 or 2 nitrogen, or oxygen atoms as hetero atoms, which comprises the steps of 1. reacting a 8-substituted-3,4-dihydrocarbostyril represented by the formula (VII)

wherein R represents a hydrogen atom or an alkyl group having 1 to 4 carbon atoms with a haloacetyl halide in the presence or absence of a solvent and in the presence of a Lewis acid catalyst to prepare a 5-haloacetyl-8-substituted-3,4-dehydrocarbostyril derivative represented by the formula (IV)

wherein R is as defined above and X represents a halogen atom, 2. reacting the resulting 5-haloacetyl-8-substituted-3,4-dihydrocarbostyril derivative represented by the formula (IV) with an amine represented by the formula (III)

wherein A is as defined above, in the presence or absence of a solvent to prepare a 5-(heterocyclic amino)acetyl-8-alkoxy (or 8-hydroxy)-3,4-dihydrocarbostyril derivative represented by the formula (IIa) or (IIb)

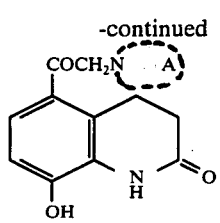
(IIb)

wherein "Alkyl" represents an alkyl group having 1 to 4 carbon atoms and A is as defined above, dealkylating the resulting 8-alkoxy derivative represented by the formula (IIa) with a hydrogen halide to produce the 5-(heterocyclic amino)aminoacetyl-8-hydroxy-3,4-dihydrocarbostyril represented by the formula (IIb), and 3. reducing the resulting 5-(heterocyclic amino)acetyl-8-hydroxy-3,4-dihydrocarbostyril derivative represented by the formula (IIb) with hydrogen in the presence of a hydrogenation catalyst or with a reducing agent.

DETAILED DESCRIPTION OF THE INVENTION

The 5-[1-hydroxy-2-(heterocyclic amino)]ethyl-8-hydroxy-3,4-dihydrocarbostyril derivatives of the formula (I) and the salts thereof are novel compounds and exhibit a β-adreno-receptor stimulating activity and, therefore, are useful as a bronchodilator, a peripheral vasodilator or an antihypertensive agent, particularly for treating bronchial asthma.

The term "alkyl" as used herein means a straight or branched chain alkyl group having 1 to 4 carbon atoms, and includes, for example, a methyl, ethyl, propyl, isopropyl, butyl, sec-butyl, tert-butyl group and the like.

The term "aralkyl" as used herein means an aralkyl group containing a straight or branched chain alkyl moiety having 1 to 4 carbon atoms, for example, a benzyl, α-methylbenzyl, α,α-dimethylbenzyl, phenethyl, α,α-dimethylphenethyl group and a like group.

The term "6-membered substituted or unsubstituted heterocyclic ring" as used herein means heterocyclic groups containing 1 or 2 nitrogen, or oxygen atoms as hetero atoms such as morpholino, piperazino, or a like group which can be unsubstituted or substituted with an alkyl group having 1 to 4 carbon atoms, such as a methyl, ethyl, isopropyl, tert-butyl group and the like, for example, a 2-methylpiperazino, 3-methylpiperazino, 4-methylpiperazino, 2-ethylpiperazino, 3-ethylpiperazino, 4-ethylpiperazino, 2-isopropylpiperazino, 3-isopropylpiperazino, 4-isopropylpiperazino, 2-methylmorpholino, 3-methylmorpholino, 2-isopropylmorpholino, 3-isopropylmorpholino group and the like.

The term "halogen" as used herein includes fluorine, chlorine, bromine and iodine, preferably chlorine and bromine.

The compounds of the present invention represented by the formula (I) can be prepared from an 8-substituted-3,4-dihydrocarbostyril according to the following reaction scheme:

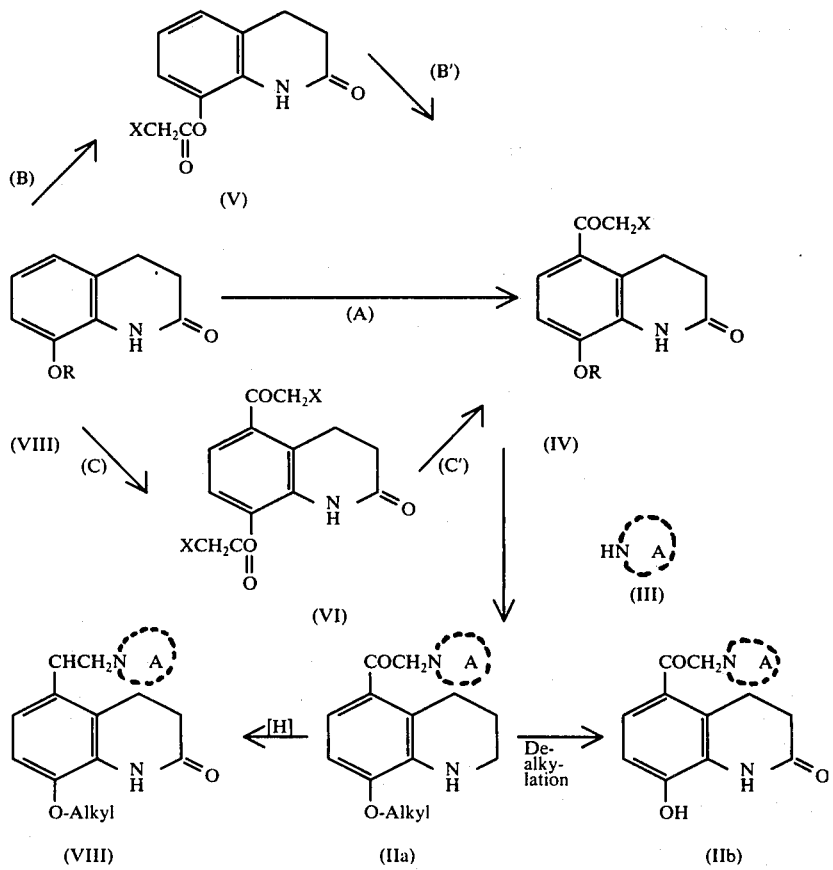

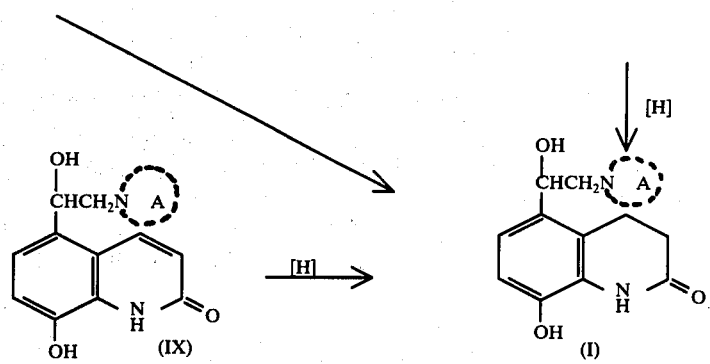

wherein R represents a hydrogen atom or an alkyl group having 1 to 4 carbon atoms; A, when taken together with the nitrogen atom to which it is attached, form a 6-membered substituted or unsubstituted heterocyclic ring containing 1 or 2 nitrogen, or oxygen atoms as hetero atoms; and X represents a halogen atom.

The 8-substituted-3,4-dihydrocarbostyril of the formula (VII) used as a starting material in the preparation of the compounds of the formula (IV) is a known compound and can easily be prepared by, for example, the method as disclosed in J. D. Loudon and J. Ogg; *J. Chem. Soc.*, 1955, 739 or Fritz Mayer, L. van Zutphen and H. Philips, *Ber.*, 60, 858 (1927).

As illustrated in the above reaction scheme, the 5-haloacetyl-8-substituted-3,4-dihydrocarbostyril represented by the formula (IV) which is an intermediate in the process of this invention can be prepared in one step by reacting the corresponding 8-substituted-3,4-dihydrocarbostyril of the formula (VII) with a haloacetyl halide in the absence or presence of a solvent and in the presence of a Lewis acid catalyst (route A).

The compound of the formula (IV) wherein R is a hydrogen atom can also be prepared by any of the alternative routes (B)+(B') and (C)+(C') starting from 8-hydroxy-3,4-dihydrocarbostyril of the formula (VII) wherein R is a hydrogen atom.

In the route (B)+(B'), the reaction between the 8-hydroxy-3,4-dihydrocarbostyril (VII) and the haloacetyl halide results in the production of a novel 8-haloacetoxy-3,4-dihydrocarbostyril of the formula (V)

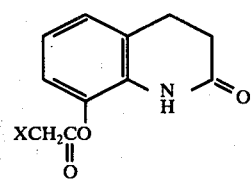
(V)

wherein X is a halogen atom, which is then subjected to the rearrangement of the haloacetyl group to form the intermediate of the formula (IV).

In the route (C)+(C'), the reaction between the starting material (VII) and the haloacetyl halide results in the production of a novel 5-haloacetyl-8-haloacetoxy-3,4-dihydrocarbostyril of the formula (VI)

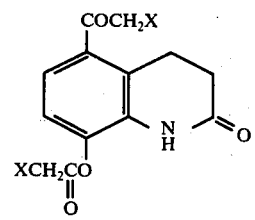
(VI)

wherein X is as defined above, which is then subjected to hydrolysis of the 8-haloacetyl group to form the intermediate of the formula (IV).

In practice, the reaction between the 8-hydroxy-3,4-dihydrocarbostyril and the haloacetyl halide proceeds via a combination of the above described three reaction routes, (A), (B)+(B') and (C)+(C'). Therefore, the reaction product is obtained as a mixture of the compounds of the formulae (IV), (V) and (VI). Generally, when the reaction is conducted at relatively low temperatures, the resulting product is a mixture of the compounds of the formulae (IV) and (V) with a small amount of the compound of the formula (VI), whereas if the reaction is conducted at relatively high temperatures, the resulting product is a mixture of the compounds of the formulae (IV) and (VI) with a small amount of the compound of the formula (V).

Isolation of the compound of the formulae (IV), (V) or (VI) from the reaction product can be advantageously carried out by well known procedures, for example, by fractional crystallization.

In a preferred embodiment for isolation, after completion of the reaction, the solvent used is removed by distillation to obtain a residue or the reaction mixture is poured into crushed ice to precipitate crystals. The residue or the crystals are washed with hot water or cool methanol. The insoluble substances are recrystallized from methanol to obtain the 5-haloacetyl-8-hydroxy-3,4-dihydrocarbostyril of the formula (IV). The residual methanolic mother liquor is concentrated to dryness under reduced pressure, and the residue is recrystallized from acetone to obtain the 8-haloacetoxy-3,4-dihydrocarbostyril of the formula (V). The resulting acetone mother liquor is then concentrated to dryness under reduced pressure, and the residue is recrystallized from acetone or ethyl acetate to obtain the 5-haloacetyl-8-haloacetoxy-3,4-dihydrocarbostyril of the formula (VI).

The thus obtained 5-haloacetyl-8-substituted-3,4-dihydrocarbostyril intermediate (when R is an alkyl group, a 5-haloacetyl-8-alkoxy-3,4-dihydrocarbostyril and when R is a hydrogen atom, a 5-haloacetyl-8- hydroxy-3,4-dihydrocarbostyril) of the formula (IV) is then reacted with a heterocyclic organic amine represented by the formula (III)

  (III)

wherein A is as defined above, in the presence or absence of a solvent to obtain a 5-(heterocyclic amino)acetyl-8-substituted-3,4-dihydrocarbostyril derivative represented by the formula (II)

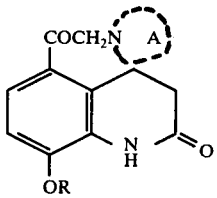  (II)

wherein R, and A are as defined above, i.e., when R is an alkyl group, a 5-(heterocyclic amino)acetyl-8-alkoxy-3,4-dihydrocarbostyril derivative represented by the formula (IIa)

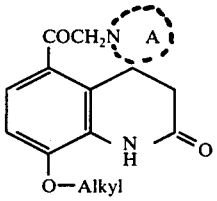  (IIa)

wherein "Alkyl" represents an alkyl group having 1 to 4 carbon atoms and A is as defined above, or, when R is a hydrogen atom, a 5-(heterocyclic amino)acetyl-8-hydroxy-3,4-dihydrocarbostyril represented by the formula (IIb)

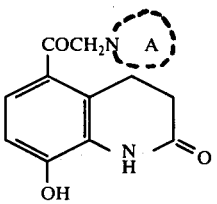  (IIb)

wherein A is as defined above.

The 8-alkoxy compound of the formula (IIa) as obtained above can then be dealkylated with a hydrogen halide such as hydrogen bromide to form the corresponding 8-hydroxy compound of the formula (IIb)

The 5-[1-hydroxy-2-(heterocyclic amino)]ethyl-8-hydroxy-3,4-dihydrocarbostyril derivative of the formula (I) of the present invention can be prepared by reducing the above obtained 5-(heterocyclic amino)acetyl-8-hydroxy-3,4-dihydrocarbostyril derivative of the formula (IIb).

Both the compounds (IIb) and the compounds (I) of the present invention are novel compounds.

The process according to the present invention will be hereinafter illustrated in greater detail.

The haloacetyl halide which is used in the present invention as a reactant in the preparation of the compound of the formula (IV) includes those having a chlorine, bromine, iodine or fluorine atom as the halogen atom, with chloroacetyl chloride being preferred.

In the reaction route (A), the catalyst which can be used is a usual Lewis acid, for example, aluminum chloride, aluminum bromide, zinc chloride, ferric chloride, stannic chloride, boron trifluoride, titanium chloride and the like, with aluminum chloride being preferably used. The catalyst is used in an amount of from about 2 to about 10 moles, preferably 3 to 6 moles, per mole of the 8-substituted-3,4-dihydrocarbostyril of the formula (VII).

This reaction can be effected in the absence of a solvent but the reaction proceeds more smoothly in an inert organic solvent. Suitable examples of inert organic solvents which can be used in this reaction are carbon disulfide, nitrobenzene, diethyl ether, dioxane and the like, preferably, carbon disulfide. These inert organic solvents are usually used in a volume of 0.5 to 20, preferably 2 to 10 times the volume of the reactants. The reaction can be advantageously carried out under anhydrous condition.

Reaction (A) is generally conducted using an equimolar amount to a large excess of the haloacetyl halide, preferably about 2 to about 20 moles, most preferably 2 to 10 moles, of the haloacetyl halide per mole of the 8-substituted-3,4-dihydrocarbostyril of the formula (VII). The reaction proceeds at room temperature (about 20° to 30° C) to about 150° C, preferably room temperature to 80° C. The reaction time varies depending upon the reaction temperature employed, but it is usually from about 1 to about 20 hours, preferably 1 to 10 hours.

Reaction (B) can be carried out using the same amount of the same catalyst as used in reaction (A) with same solvent as used in reaction (A) or without any solvent. This reaction can be carried out using an equimolar amount to a large excess amount of the haloacetyl halide, preferably from about 2 to about 20 moles, most preferably 2 to 10 moles, per mole of the 8-substituted-3,4-dihydrocarbostyril of the formula (VII) at a temperature of about room temperature to about 150° C, preferably from room temperature to 80° C, for about 1 to about 20 hours, preferably 1 to 10 hours.

Reaction (B') to obtain a 5-haloacetyl-8-substituted-3,4-dihydrocarbostyril of the formula (IV) from the 8-haloacetoxy-3,4-dihydrocarbostyril of the formula (V) obtained in reaction (B) as above described is generally known as a Fries rearrangement, and can be carried out using the same catalyst as in reaction (A) in an amount of about 2 to about 10 moles, preferably 3 to 6 moles, per mole of the compound of the formula (V) with the same solvent as in reaction (A) or without any solvent. The reaction temperature ranges from room temperature to about 150° C, preferably room temperature to 80° C and the reaction time ranges from about 1 to about 20 hours, preferably 1 to 10 hours. This reaction can proceed in the presence of any haloacetyl halide which remains unreacted in the previous reaction system (B). In such a case, it was found that the presence of the haloacetyl halide improves the yield of the product, the 5-haloacetyl-8-substituted-3,4-dihydrocarbostyril of the formula (III).

Reaction (C) can be carried out using the same amount of the same catalyst as used in reaction (A) in the same solvent as used in reaction (A) or without any solvent. The haloacetyl halide is used in an equimolar amount to a large excess relative to the 8-substituted-3,4-dihydrocarbostyril of the formula (VII), but preferably in an amount of about 2 to about 20 moles, most preferably 2 to 10 moles, per mole of the 8-substituted- 3,4-dihydrocarbostyril of the formula (VII). The reaction temperature is from about room temperature to about 150° C, preferably room temperature to 80° C, and the reaction time is from about 1 to about 20 hours, preferably 1 to 10 hours.

Reaction (C') to obtain the compound of the formula (IV) from the above obtained 5-haloacetyl-8-haloacetoxy-3,4-dihydrocarbostyril of the formula (VI) can be conducted using a catalyst, for example, a basic substance such as an alkali metal hydroxide or carbonates, e.g., sodium hydroxide, potassium hydroxide, sodium carbonate, potassium carbonate and the like or an inorganic acid, e.g., hydrochloric acid, sulfuric acid, phosphoric acid and the like in the presence of a solvent, for example, water, a lower alcohol such as ethanol, methanol, isopropanol and the like. The amount of the catalyst varies depending upon the type of the catalyst used. For example, hydrochloric acid or sodium hydroxide and the like is used in an amount of from about 1 to 5 moles per mole of the 5-haloacetyl-8-haloacetoxy-3,4-dihydrocarbostyril of the formula (VI). The reaction generally proceeds at a temperature of about 0° to about 150° C for about 0.5 to about 5 hours, but it is advantageous to carry out the reaction at a temperature of from 0° to 40° C when a basic substance is used as a catalyst and at a temperature of 70° to 100° C when an inorganic acid is used as a catalyst.

The amines of the formula (III) which can be used as a reactant in the preparation of the 5-(heterocyclic amino)acetyl-8-substituted-3,4-dihydrocarbostyril derivative of the formula (IIb) or (IIa) include substituted or unsubstituted heterocyclic amines, for example, morpholine, 2-methylmorpholine, 3-methylmorpholine, 2-ethylmorpholine, 3-ethylmorpholine, 2-isopropylmorpholine, 3-isopropylmorpholine, piperazine, 2-methylpiperazine, 3-methyl-piperazine, 4-methylpiperazine, 2-ethylpiperazine, 3-methylpiperazine, 4-methylpiperazine and the like.

The reaction between the 5-haloacetyl-8-substituted-3,4-dihydrocarbostyril intermediate of the formula (IV) and the amine of the formula (III) can be carried out in the absence of a solvent since the amine of the formula (IV) per se also serves as a solvent but it is advantageous to conduct this reaction in an appropriate solvent. Suitable examples of solvents which can be used in this reaction include lower alcohols such as methanol, ethanol, isopropanol and the like, ethers such as dioxane, diethyl ether and the like, esters such as ethyl acetate, aromatic hydrocarbons such as benzene, toluene, xylene and the like, nitrile solvents such as acetonitrile and the like. Ethanol and isopropanol are preferred.

This reaction can be effected using an equimolar amount to, especially in the absence of the solvent, a large excess amount of the amine of the formula (III), preferably from about 2 to about 10 moles of the amine per mole of the 5-haloacetyl-8-substituted-3,4-dihydrocarbostyril of the formula (IV), at room temperature to a refluxing temperature of the reaction system, preferably 40° to 100° C, at about atmospheric pressure to about 10 atms.

Thus, when the 8-hydroxy-3,4-dihydrocarbostyril is used as a starting material, the 5-(heterocyclic amino)acetyl-8-hydroxy-3,4-dihydrocarbostyril of the formula (IIb) is obtained, which can be subjected to the subsequent reduction reaction. When the 8-alkoxy-3,4-dihydrocarbostyril of the formula (VII) wherein R is an alkyl group is used as a starting material, the corresponding 5-(heterocyclic amino)acetyl-8-alkoxy-3,4-dihydrocarbostyril of the formula (IIa) is obtained. The resulting 5-(heterocyclic amino)-acetyl-8-alkoxy-3,4-dihydrocarbostyril (IIa) is then reacted with a hydrogen halide to dealkylate the 8-position of the carbostyril moiety thereby obtaining the compound (IIb).

The hydrogen halides used in this dealkylation include, for example, hydrogen bromide, hydrogen chloride, hydrogen iodide and the like, preferably hydrogen bromide. These hydrogen halides can advantageously be employed in an appropriate solvent such as methanol, ethanol, isopropanol, preferably water, in a form of an about 10 to 50%, preferably 47%, aqueous solution of hydrogen bromide.

This dealkylation reaction can generally be carried out using the hydrogen halide in an equimolar amount to, preferably, a large excess with respect to the compound (IIa) by heating at a temperature of from about 100° to about 150° C, preferably at reflux, for about 1 to about 20 hours, preferably 3 to 10 hours.

The reduction of the above obtained 5-(heterocyclic amino)acetyl-8-hydroxy-3,4-dihydrocarbostyril derivative of the formula (IIb) to a 5-[1-hydroxy-2-(heterocyclic amino)]ethyl-8-hydroxy-3,4-dihydrocarbostyril derivative of the formula (I) can be conducted by a conventional reduction using a reducing agent such as lithium aluminum hydride, sodium borohydride and the like, or a conventional catalytic reduction with hydrogen in the presence of a hydrogenation catalyst such as palladium black, palladium-on-carbon, Raney nickel, platinum black, platinum oxide and the like.

The above reducing agent can be used in an amount of from about 2 to about 10 moles, preferably 2 to 5 moles, per mole of the carbostyril compound of the formula (IIb) in a solvent while cooling under atmospheric presure at a temperature of from about 0° to about 100° C, preferably 20° to 50° C. When sodium borohydride is used as a reducing agent, the solvent is preferably water or alcohols such as methanol, ethanol and the like, and when lithium aluminum hydride is used as a reducing agent, the solvent is preferably a non-aqueous solvent such as anhydrous diethyl ether, ethyl acetate, tetrahydrofuran and the like.

The catalytic reduction can be carried out using the above catalyst in an amount of from about 0.05 to about 1 mole, preferably 0.1 to 0.5 mole, per mole of the carbostyril compound of the formula (IIb) in a solvent, for example, water or an alcohol such as methanol, ethanol or isopropanol under a hydrogen atmosphere at a pressure of from about atmospheric pressure to about 100 atms., preferably 1 to 50 atms., at a temperature of from room temperature to about 150° C, preferably from room temperature to 120° C, advantageously with agitation of the reduction system. It is advantageous to carry out the above catalytic reduction at a temperature higher than about 50° C at atmospheric pressure or at a temperature higher than room temperature under pressure.

Alternatively, the compound of the formula (I) of the present invention can also be prepared by reducing the previously prepared 5-(heterocyclic amino)acetyl-8-alkoxy-3,4-dihydrocarbostyril derivative of the formula (IIa) in the same manner as described above with respect to the reduction of the compound of the formula (IIb) to a 5-[1-hydroxy-2-(heterocyclic amino)]ethyl-8-alkoxy-3,4-dihydrocarbostyril derivative having the formula (VIII)

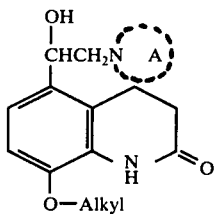

(VIII)

wherein A and "Alkyl" are as defined above, which is then dealkylated with a hydrogen halide such as hydrogen bromide in the same manner as described above with respect to the dealkylation from the compound (IIa) to the compound (IIb).

Further, the compound of the formula (I) can also be prepared by reducing the corresponding 5-(heterocyclic amino)-acetyl-8-hydroxycarbostyril derivative having the formula (IX)

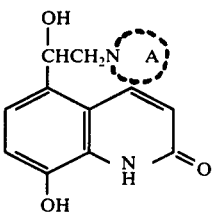

(IX)

wherein A is as defined above.

The 5-(heterocyclic amino)acetyl-8-hydroxycarbostyril derivatives of the formula (IX) which can be used as a reactant in the above described reduction can be obtained according to the process as disclosed in applicants' co-pending U.S. patent application Ser. No. 536,705, filed Dec. 26, 1974.

The reduction above can be conducted under the same conditions as described above with respect to the reduction of the compound of the formula (IIb) in the presence of the same catalyst as used therein.

Both the compounds of the formula (II) and the compounds of the formula (I) as obtained above are basic substances and can form acid addition salts with various organic or inorganic acids. Particularly useful such salts are the pharmaceutically acceptable acid addition salts formed with inorganic acids such as hydrochloric acid, sulfuric acid, phosphoric acid, hydrobromic acid, etc. or organic acids such as oxalic acid, maleic acid, fumaric acid, malic acid, tartaric acid, citric acid, ascorbic acid, etc. These acid addition salts can easily be prepared by well-known procedures, for example, by adding an equimolar to an excess amount of the acid to a solution of the compound dissolved in an appropriate organic solvent such as methanol, ethanol, iso-propanol, acetone and the like.

Both the free bases of the compounds of the formula (I) and acid addition salts thereof exhibit a stimulating activity on β-adreno-receptor and, therefore, are very useful as pharmaceuticals for treating disorders such as bronchial asthma. As is apparent to one skilled in the art, the compounds of the present invention contain two asymmetrical centers and, therefore, can be present in four optically active forms.

Particularly preferred compounds of the formula (I) are the following basic compounds and their hydrochlorides, sulfates, phosphates, maleates, fumarates and oxalates.

5-(1-Hydroxy-2-morpholino)ethyl-8-hydroxy-3,4-dihydrocarbostyril
5-(1-Hydroxy-2-piperazine)ethyl-8-hydroxy-3,4-dihydrocarbostyril
5-[1-Hydroxy-2-(4-methylpiperazino)]ethyl-8-hydroxy-3,4-dihydrocarbostyril The present invention is further illustrated in greater detail with reference to the following Examples, but these examples are given for illustrative purposes only and are not to be construed as limiting the scope of the invention. Unless otherwise indicated, all parts, percents, ratios and the like are by weight.

EXAMPLE 1

24.3 g of 8-hydroxy-3,4-dihydrocarbostyril (VII) and 68 g of chloroacetyl chloride were added to 130 ml of carbon disulfide, and 200 g of aluminum chloride was added slowly to the mixture while stirring and cooling in ice-water. The mixture was stirred for 6 hours at a temperature of 60° to 70° C and carbon disulfide was distilled off. The resulting residue was poured into 500 ml of ice-water. The precipitated crystals were filtered, washed with water and recrystallized twice from methanol to give 8.0 g of 5-chloroacetyl-8-hydroxy-3,4-dihydrocarbostyril (IV) as light yellow crystals having a melting point of 189° to 191° C.

EXAMPLE 2

13 g of 8-hydroxy-3,4-dihydrocarbostyril (VII) and 20 g of chloroacetyl chloride were dissolved in 100 ml of nitrobenzene, and 40 g of aluminum chloride was added slowly to the mixture followed by stirring for 15 hours at a temperature of 70° to 75° C. The mixture was then steam-distilled to remove nitrobenzene. After allowing the mixture to cool, the precipitated crystals were filtered, washed with hot water and recrystallized from methanol to give 7.2 g of 5-chloroacetyl-8-hydroxy-3,4-dihydrocarbostyril (IV) as light yellow crystals having a melting point of 189° to 190° C.

EXAMPLE 3

66 g of chloroacetyl chloride and 30 ml of nitrobenzene were added to 17 g of 8-methoxy-3,4-dihydrocarbostyril (VII), and 100 g of aluminum chloride was added slowly to the resulting mixture while cooling with ice followed by stirring for 30 minutes at room temperature. After allowing the mixture to stand for additional 30 minutes, the mixture was poured into 700 ml of icewater. The precipitate thus formed was filtered, washed with ethanol and recrystallized from methanol to give 20 g of white needle-like crystals having a melting point of 187° to 188° C. The crystals thus obtained was confirmed by NMR and IR spectra and elemental analysis as 5-chloroacetyl-8-methoxy-3,4-dihydrocarbostyril (IV).

EXAMPLE 4

33 g of chloroacetyl chloride and 80 ml of carbon disulfide were added to 8.5 g of 8-methoxy-3,4-dihydrocarbostyril (VII), and 50 g of aluminum chloride was added slowly to the resulting mixture while cooling with ice followed by stirring for 2 hours at room temperature. The carbon disulfide layer was removed by decantation, and crushed ice was added to the remaining solution to crystallize the product. The precipitated crystals thus obtained were filtered, washed with ethanol and recrystallized from methanol to give 11 g of white needle-like crystals having a melting point of 187° to 188° C. The produce thus obtained was confirmed by NMR and IR spectra and elemental analysis as 5-chloroacetyl-8-methoxy-3,4-dihydrocarbostyril (IV).

EXAMPLE 5

24.3 g of 8-hydroxy-3,4-dihydrocarbostyril (VII) and 68 g of chloroacetyl chloride were added to 130 ml of carbon disulfide, and 200 g of aluminum chloride was added slowly to the mixture while stirring and cooling with ice-water. The resulting mixture was then allowed to react for 4 hours under ice-cooling to give 8-chloroacetoxy-3,4-dihydrocarbostyril (V). The reaction mixture was stirred for 2 hours at a temperature of 60° to 70° C and carbon disulfide was distilled off. The resulting residue was poured into 500 ml of ice-water and the precipitated crystals were filtered, washed with water and recrystallized twice from methanol to give 8.0 g of 5-chloroacetyl-8-hydroxy-3,4-dihydrocarbostyril (IV) as light yellow crystals having a melting point of 189° to 191° C.

The 8-chloroacetoxy-3,4-dihydrocarbostyril (V) produced as an intermediate in the above procedure was isolated from an aliquot to the reaction mixture and found to have a melting point of 183° to 186° C after recrystallization from acetone.

EXAMPLE 6

40 g of aluminum chloride was added to 11.5 g of 8-hydroxy-3,4-dihydrocarbostyril (VII), and the mixture was thoroughly stirred. 21 g of chloroacetyl chloride was then added slowly to the mixture while cooling with ice-water and the resulting mixtures was stirred at a temperature of 35° to 40° C for 2 hours followed by distillation of any excess of the chloroacetyl chloride. The residue thus obtained was poured into crushed ice, and the precipitated crystals were filtered, washed with water and recrystallized from acetone to give 5.6 g of 8-chloroacetoxy-3,4-dihydrocarbostyril (V) as light yellow crystals having a melting point of 182° to 184° C.

EXAMPLE 7

13 g of 8-hydroxy-3,4-dihydrocarbostyril (VII) and 20 g of chloroacetyl chloride were dissolved in 100 ml of nitrobenzene, and 40 g of aluminum chloride was added slowly to the mixture followed by stirring at a temperature of 70° to 75° C for 15 hours. The nitrobenzene was then steam-distilled. After allowing the mixture to cool, the precipitated crystals were filtered, washed with hot water and recrystallized from methanol to give 7.2 g of 5-chloroacetyl-8-hydroxy-3,4-dihydrocarbostyril (IV) as light yellow crystals having a melting point of 189° to 190° C.

EXAMPLE 8

30 g of aluminum chloride was added slowly while ice-cooling and stirring to 6.0 g of 8-hydroxy-3,4-dihydrocarbostyril (VII) and 15.0 g of chloroacetyl chloride followed by stirring at a temperature of 55° to 60° C for 6 hours to produce 5-chloroacetyl-8-chloroacetoxy-3,4-dihydrocarbostyril (VI). 50 ml of a 10% aqueous hydrochloric acid was added to the reaction mixture which was then stirred for 3 hours at a temperature of 95° to 100° C. After allowing the mixture to cool, the precipitated crystals were filtered, washed with water and recrystallized from methanol to give 2.7 g of 5-chloroacetyl-8-hydroxy-3,4-dihydrocarbostyril (IV) as light yellow crystals having a melting point of 189° to 190° C.

In the above procedure, an aliquot of the reaction mixture was taken out from the reaction system before the hydrolysis with hydrochloric acid and poured into ice-water. The precipitated crystals were filtered, washed with hot water and recrystallized from dimethylformamide-methanol (1:1 by volume) to give 5-chloroacetyl-8-chloroacetoxy-3,4-dihydrocarbostyril (VI) as light yellow crystals having a melting point of 206° to 207° C.

EXAMPLE 9

10 g of 5-chloroacetyl-8-hydroxy-3,4-dihydrocarbostyril (IV) was suspended in 50 ml of benzene, and 10 ml of piperazine (III) was added to the suspension followed by allowing the mixture to react while heating under refluxing and stirring for 6 hours. The reaction mixture was filtered to recover the reaction product which was then washed with benzene and then with 50 ml of isopropanol. The resulting insoluble material was dissolved in 150 ml of a 2% aqueous hydrobromic acid. The solution was The structure of the material thus obtained was confirmed by NMR and IR spectra and elemental analysis.

EXAMPLE 10

2.0 g of 5-piperazinoacetyl-8-hydroxy-3,4-dihydrocarbostyril dihydrobromide (IIb) prepared as described in Example 9 was dissolved in 40 ml of water, and 0.5 g of palladium black as a catalyst was added to the solution. The mixture was stirred at a temperature of 70° to 75° C under atmospheric pressure in the presence of hydrogen gas to absorb the hydrogen. After completion of the reduction, the catalyst was filtered and the filtrate was concentrated to dryness under reduced pressure. The water remaining in the resulting residue was then completely removed ethanol, and acetone was added to the residue to crystallize the product. Recrystallization from a mixture of water and acetone gave 1.2 g of a colorless amorphous material having a melting point 243° to 246° C. The product thus obtained was confirmed by NMR and IR spectra and elemental analysis to be 5-(1-hydroxy-2-piperazino)ethyl-8-hydroxy-3,4-dihydrocarbostyril (I) dihydrobromide.

EXAMPLE 11

The same procedure as in Example 9 was conducted except that 4-methylpiperazine (III) and hydrochloric acid were used instead of piperazine and hydrobromic acid, respectively. 5.3 g of white amorphous 5-(4-methylpiperazino)acetyl-8-hydroxy-3,4-dihydrocarbostyril (IIb) dihydrochloride was obtained.

Then, using 2.0 g of 5-(4-methylpiperazino)acetyl-8-hydroxy-3,4-dihydrocarbostyril (IIb) 1.4 g of a colorless amorphous material having a melting point (dec.) of 149° to 151° C was obtained in the same way as in Example 10. The product thus obtained was confirmed by NMR and IR spectra and elemental analysis to be 5-[1-hydroxy-2-(4-methylpiperazino)]ethyl-8-hydroxy-3,4-dihydrocarbostyril (I) dihydrochloride.

EXAMPLE 12

10 g of 5-chloroacetyl-8-hydroxy-3,4-dihydrocarbostyril (IV) was suspended in 50 ml of benzene, and 10 ml of morpholine (III) was added to the suspension followed by allowing the mixture to react while heating under refluxing and stirring for 6 hours. The reaction mixture was filtered to recover the reaction product which was then washed with benzene and then with 50 ml of isopropanol. The resulting insoluble material was dissolved in 150 ml of a 2% aqueous hydrochloric acid. The solution was concentrated to dryness under reduced pressure and the resulting residue was recrystalized from ethanol to obtain 8.5 g of white amorphous 5-morpholinoacetyl-8-hydroxy-3,4-dihydrocarbostyril (IIb) hydrochloride.

The structure of the material thus obtained was confirmed by NMR and IR spectra and elemental analysis.

EXAMPLE 13

2.0 g of 5-morpholinoacetyl-8-hydroxy-3,4-dihydrocarbostyril (IIb) hydrochloride prepared as described in Example 11 was dissolved in 40 ml of water, and 0.5 g of palladium black as a catalyst was added to the solution. The mixture was stirred at a temperature of 70° to 75° C under atmospheric pressure in the presence of hydrogen gas to absorb the hydrogen. After completion of the reduction, the catalyst was filtered and the filtrate was concentrated to dryness under reduced pressure. The water remaining in the resulting residue was then completely removed ethanol, and acetone was added to the residue to crystallize the product. Recrystallization from a mixture of isopropanol and ether gave 1.1 g of a colorless amorphous material having a melting point of 145° to 146° C. The product thus obtained was confirmed by NMR and IR spectra and elemental analysis as 5-(1-hydroxy-2-morpholino)ethyl-8-hydroxy-3,4-dihydrocarbostyril (I) hydrochloride.

REFERENCE EXAMPLE

The stimulating activity of the compounds of this invention on $\beta$-adreno-receptor was determined as follows:

Male hybrid adult dogs, weighing 10 to 15 Kg were anesthesized with 30 mg/Kg of body weight of sodium pentobarbital administered intravenously. Each of the anesthesized dogs was secured on its back and a cannula was inserted into the trachea. Artificial respiration was conducted using a device according to the Knozett-Rössler method (Konzett H. & Rössler R., "Versuchungsanordnung zu Untersuchungen an der Bronchial Moskolatur", *Arch, Exp. Path., Pharmack,* 195, 71–74, 27–40 (1949)). The volume of the overflowing air at the time of inhalation was measured through a pneumotachometer to determine bronchial resistance and the values obtained were recorded on a polygraph.

In the above experiment, histamine was employed as a bronchoconstrictor at a dosage level of 10 mg/Kg of body weight, and an aqueous solution containing each of the test compounds and controls shown in Table I below was then administered to each of the anesthisized dogs through the femoral vein at the various dosage levels below 1 minute before the administration of the histamine. Sodium pentobarbital was infused during the experiment at a dosage level of 4 mg/Kg of body weight/hr. using an automatic injector in order to inhibit spontaneous respiration and to keep the anesthetic condition constant over the test period. The results ($ED_{50}$) obtained are shown in Table I below.

Table 1

| Sample | Bronchial Resistance $ED_{50}$ | $\dfrac{ED_{50} \text{ of Isoproterenol}}{ED_{50} \text{ of Sample}} \times 100$ |
| --- | --- | --- |
| 5-(1-Hydroxy-2-piperazino)ethyl- | $4.52 \times 10^{-8}$ | 184 |

Table 1-continued

| Sample | Bronchial Resistance $ED_{50}$ | $\dfrac{ED_{50} \text{ of Isoproterenol}}{ED_{50} \text{ of Sample}} \times 100$ |
| --- | --- | --- |
| 8-hydroxy-3,4-dihydrocarbostyril Hydrobromide | | |
| 5-(1-Hydroxy-2-morpholino)ethyl-8-hydroxy-3,4-dihydrocarbostyril Hydrochloride | $3.66 \times 10^{-8}$ | 228 |
| Isoproterenol | $8.35 \times 10^{-8}$ | 100 |

From the results shown in Table 2 it is apparent that the compounds of this invention have $ED_{50}$ values about ½ times as small as that of isoproterenol, which means the former compounds are superior over the latter compounds as a $\beta$-adrenergic stimulating agent.

In order to investigate side effects of the above-described test compounds, $ED_{30}$, which corresponds to effects on atria, of the respective compounds were determined using guinea pig atria as follows:

Right atria were excised from male Hartley strain guinea pigs weighing 450 to 600 g, and suspended in a 30 ml tissue bath containing Lock solution maintained at 36° C and aerated with 95% $O_2$ — 5% $CO_2$. Spontaneous contraction rate was obtained from isometric recordings using force transducers (San-ei Sokki, Type 45072). The resting tension was maintained at 0.5 g for each atria. The test compounds as shown in Table 1 were added to bath fluid at a single dose for each response.

Effective doses ($ED_{30}$ values) of the test compound which induced 30 beats/min. increase in contractile rate were determined and compared with that of isoproterenol.

The results obtained are shown in Table 2.

Table 2

| Sample | Side Effect $ED_{30}$ | $\dfrac{ED_{30} \text{ of Isoproterenol}}{ED_{30} \text{ of Sample}} \times 1{,}000$ |
| --- | --- | --- |
| 5-(1-Hydroxy-2-piperazino)-ethyl-8-hydroxy-3,4-dihy-drocarbostyril Hydrobromide | $2.78 \times 10^{-9}$ | 72 |
| 5-(1-Hydroxy-2-morpholinol-ethyl-8-hydroxy-3,4-dihydrocarbostyril Hydrochloride | $3.21 \times 10^{-9}$ | 62 |
| Isoproterenol | $2.0 \times 10^{-10}$ | 1,000 |

From the results shown in Table 2 it is clear that the side effect of the compound of this invention is much less, than that of Isoproterenol.

Further, the acute toxicity was determined with respect to the test compounds shown in Table 3 below using 5 to 6 groups each containing 10 male rats (dd strain; body weight, 18 to 22 g) which had been fasted for 12 hours prior to the test. Isoproterenol was used as a control. The $LD_{50}$ (50% lethal dose) results are as follows.

Table 3

| Compound | $LD_{50}$ (mg/Kg) i.v. |
| --- | --- |
| 5-(1-Hydroxy-2-piperazino)-ethyl-8-hydroxy-3,4-dihydrocarbostyril Hydrobromide | 101 (90-133) |

Table 3-continued

| Compound | $LD_{50}$ (mg/Kg) i.v. |
|---|---|
| 5-(1-Hydroxy-2-morpholino)-ethyl-8-hydroxy-3,4-dihydro-carbostyril Hydrochloride | 112 (96–140) |
| Isoproterenol | 94 (78–121) |

From the results shown in Table 3, it can be seen that $LD_{50}$ values of the compounds of the present invention are substantially the same as or slightly improved as compared with those of isoproterenol.

In view of the results shown in Tables 1 to 3, it is concluded that the compounds of this invention are highly improved in their side effects, while they have a good β-adrenergic stimulating activity, with the toxicity remains substantially the same as or slightly improved as compared with those exhibited by the conventional compound.

The compounds of the present invention can be administered at a dosage level of from 100 to 50 mg/kg/day by oral, intravenous, intramuscular, intrarectal or inhalation administration in a conventional pharmaceutical dosage form such as a tablet, powder, granule, capsule, syrup, solution, suspension, inhalant (aerosol spray), suppository and the like, preferably, in combination with pharmaceutically acceptable carriers or diluents which are well known in the art.

Pharmaceutical compositions generally comprise at least one compound of the present invention and pharmaceutical carriers or diluents which are commonly employed in conventional pharmaceutical compositions. The composition may contain other active components which do not adversely affect the activities of the compounds of this invention.

Suitable pharmaceutical carriers or diluents include solid carriers such as corn starch, calcium sulfate dihydrate, magnesium stearate, lactose, Aerosil (tradename of Nihon Aerosil Co., Ltd. Japan) and the like which are suitable for use in oral, suppository, injectable and inhalant formulations. The oral dosage forms can be formulated in accordance with well known procedures and conveniently formulated into tablets which can be optionally provided with a sugar coating. A soluble tablet which is suitable for sublingual administration, i.e., troche or lozenge, can also be prepared.

The injectable composition can be prepared using physiologically acceptable carriers or diluents in the form of solution, suspension or dry preparation which is reconstituted instantaneously with a vehicle for injection just before administration.

The compounds of the present invention are advantageously administered in the form of an aerosol spray formulation by inhalation.

Typical examples of suitable formulations are given below, but it is to be noted that other dosages forms can also be prepared using other compounds of this invention according to the well-established pharmaceutical techniques.

FORMULATION 1

Tablets each containing the following components were prepared from the following components:

| Component | Amount |
|---|---|
| 5-(1-Hydroxy-2-piperazino)ethyl-8-hydroxy-3,4-dihydrocarbostyril | 1 mg |
| Corn Starch | 70 mg |
| Magnesium stearate | 9 mg |
| Lactose | 20 mg |
| Total | 100 mg |

FORMULATION 2

Tablets each containing the following components were prepared from the following components:

| Compounent | Amount |
|---|---|
| (5-(1-Hydroxy-2-morpholino)ethyl-8-hydroxy 3,4-dihydrocarbostyril | 1 mg |
| Corn Starch | 70 mg |
| Magnesium stearate | 9 mg |
| Lactose | 20 mg |
| Total | 100 mg |

FORMULATION 3

Aerosol spray for inhalation containing the following components per each dose was prepared and filled in the aerosol dispenser:

| Components | Amount |
|---|---|
| (5-(1-Hydroxy-2-piperazino)ethyl-8-hydroxy-3,4-dihydrocarbostyril | 50 mcg |
| Oleic Acid | 10 mcg |
| Dichlorodifluoromethane | 57 mcg |
| Trichlorofluoromethane | 25 mcg |

FORMULATION 4

Aerosol spray for inhalation containing the following components per each dose was prepared and filled in the aerosol dispenser:

| Components | Amount |
|---|---|
| 5-(1-Hydroxy-2-morpholino)ethyl-8-hydroxy-3,4-dihydrocarbostyril | 50 mcg |
| Oleic Acid | 10 mcg |
| Dichlorodifluoromethane | 57 mcg |
| Trichlorofluoromethane | 25 mcg |

While the present invention has been described in detail with reference to specific embodiments thereof, it is apparent to one skilled in the art that various changes and modifications can be made therein without departing from the spirit and the scope of the present invention.

What is claimed is:

1. A 5-[1-hydroxy-2-(heterocyclic amino)]ethyl-8-hydroxy-3,4-dihydrocarbostyril compound represented by the formula (I)

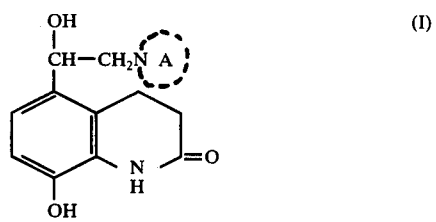

wherein A, when taken together with the nitrogen atom to which it is attached, forms a 6-membered heterocyclic ring selected from the group consisting of piperazino and morpholino, said heterocyclic ring being unsubstituted or substituted with an alkyl group having one to four carbon atoms.

2. 5-(1-Hydroxy-2-piperazino)ethyl-8-hydroxy-3,4-dihydrocarbostyril according to claim 1.

3. 5-(1-Hydroxy-2-morpholino)ethyl-8-hydroxy-3,4-dihydrocarbostyril according to claim 1.

4. 5-[1-Hydroxy-2-(4-methylpiperazino)]ethyl-8-hydroxy-3,4-dihydrocarbostyril according to claim 1.

* * * * *